United States Patent [19]

Scott

[11] 4,204,321

[45] May 27, 1980

[54] DENTAL POST

[76] Inventor: Edward S. Scott, 1818 S. Cincinnati, Tulsa, Okla. 74119

[21] Appl. No.: 889,723

[22] Filed: Mar. 24, 1978

[51] Int. Cl.² ............................................. A61C 13/00
[52] U.S. Cl. .................................................... 433/177
[58] Field of Search ............................ 32/2, 10 A, 13

[56] References Cited

U.S. PATENT DOCUMENTS

| | | | |
|---|---|---|---|
| 2,112,007 | 3/1938 | Adams | 32/2 |
| 2,609,604 | 9/1952 | Sprague | 32/10 A |

*Primary Examiner*—Robert Peshock
*Attorney, Agent, or Firm*—Head & Johnson

[57] ABSTRACT

This invention involves a novel dental post having a groove provided thereon which facilitates the seating of the denture on the dental post, eases the masticatory load on the tooth root, and increases the retentive capabilities of the dental post.

8 Claims, 7 Drawing Figures

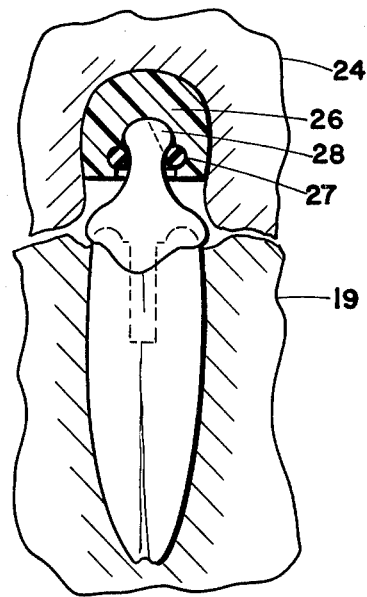
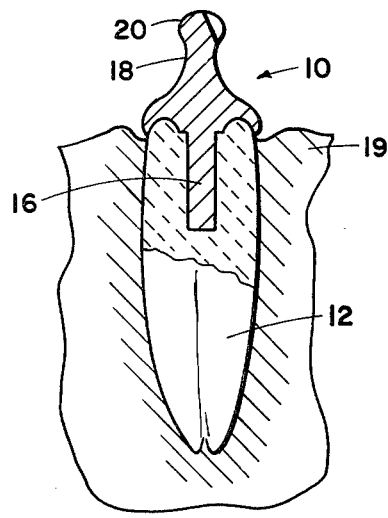
Fig. 3
Fig. 4
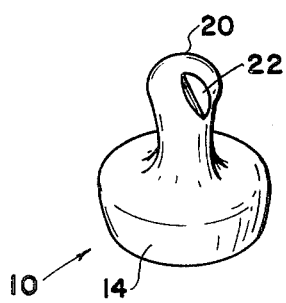
Fig. 2
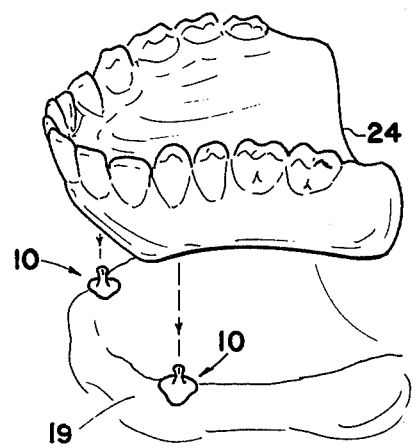
Fig. 1

4,204,321

DENTAL POST

BACKGROUND OF THE INVENTION

1. Field of the Invention

This invention refers to means of attaching a denture in the mouth of a person. It is particularly related to facilitating the seating of the denture, providing cushioning means to ease the masticatory load and further to enhance the retention of the denture.

2. Description of the Prior Art

Dentures of many types are in widespread use today and include both partial and full dentures. The retention of a partial denture is simple as the existing teeth provide the needed anchorage. Where few teeth remain and a full denture is needed, the remaining teeth may be insufficient anchorage. In such cases selected tooth roots are endodontically treated and equipped with dental posts. A dental post is usually a longitudinal abutment arising from the mandible or jaw bone and beyond the gingival or gum and carrying an enlarged head member. A complementary female recess defined in part by an elastomeric member having an opening therethrough generally an "O" ring, is housed in the denture to be secured in the mouth. The elastomeric member or "O" ring receives the head member by compression of the leastomeric member whereby the elastomeric member applies retentive force to the head member thereby securing the denture in place.

The prior art presents difficulties insofar that as the head member of the dental post is being received in the recess of the denture, fluid present in the recess is trapped therein, hindering entry and impairing the retention of the denture.

SUMMARY OF THE INVENTION

The present invention provides a novel device for securing a denture in position in a manner for overcoming the foregoing disadvantages. The novel device comprises a dental post having a head member provided with a groove which provides a passageway for fluid trapped in the recess of the denture during the seating process.

In a variation of this invention, the groove is positioned on the head member to reside within the recess of the denture whereby the airtight seal at the base of the head member made by the denture apparatus elastomeric member causes the fluid retained in the groove to be trapped therein providing a cushion to ease the masticatory load on the head member as well as enhancing the retentive capabilities of the dental post.

In still another embodiment, a circumferential groove, dimensioned to engage and anchor the elastomeric member, is provided at a position on the dental post to cause a residual space between the head member and the recess of the denture. The residual space traps fluid and thereby provides cushioning means to ease the masticatory load on the head member and enhance the retentive capabilities of the dental post.

BRIEF DESCRIPTION OF THE DRAWINGS

FIG. 1 is a perspective view of a full denture in spaced relation to the mandible or jaw bone provided with two dental posts and illustrates how the full denture seats on the dental posts.

FIG. 2 is a perspective view of a dental post embodying the invention.

FIG. 3 is a sectional elevational view of a mandible showing an endodontically prepared tooth root and having a dental post embodying the invention.

FIG. 4 is a sectional view partly in elevation of a tooth root carrying a dental post embodying the invention residing securely in a complementary recess provided in the denture to be seated thereon.

DESCRIPTION OF THE PREFERRED EMBODIMENT

First Embodiment

Figure 7:
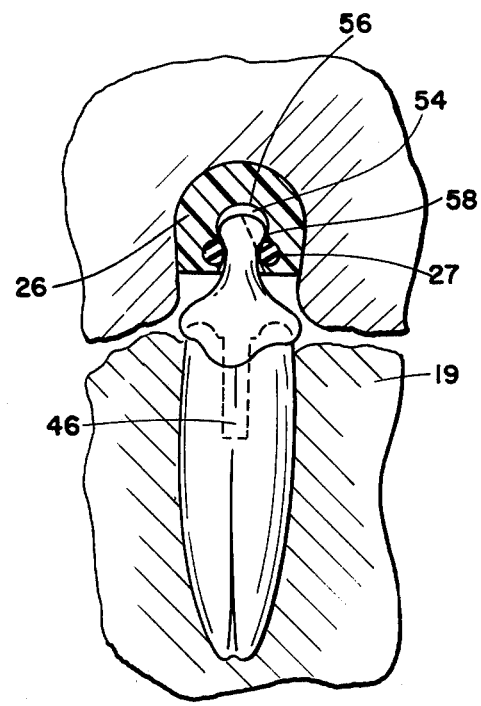
FIG. 7 is a sectional view partly in elevation of a tooth root carrying a dental post of FIG. 6 residing securely in a complementary recess provided in the denture to be seated thereon.

Referring to the drawings in detail, reference character 10 generally indicates a dental post adapted to be embedded in a tooth root 12 and comprises a substantially circular or disc-shaped main body portion 14 having a first stem member 16 extending axially outwardly therefrom in one direction for insertion into the tooth root 12 as will be hereinafter set forth. A second stem member 18 extends axially outwardly from the body 14 and in an opposite direction with respect to the stem 16 and is provided with a bulbous or enlarged head member 20 at the outer or exposed end thereof.

The head member 20 is substantially spherical in configuration and is provided with a groove 22 disposed angularly therein with respect to the axis of the second stem member 18, said axis preferably being perpendicular to the plane of the main body 14, but not limited thereto.

The dental post 10 is anchored rigidly to the tooth root 12 which has been endodontically prepared in the customary manner for receiving the first stem 16. The main body 14 is made to overlap and seal the tooth root in the customary or well-known fashion. The second stem 18 protrudes from the mandible and beyond the gingival or gum 19 to be received in a complementary recess 26 provided in the denture 24 to be seated thereon. The recess 26 is defined in part by an elastomeric member 27 having an opening therethrough wherein the head member 20 is received by compression of the elastomeric member 27 whereby the elastomeric member 27 applies retentive force to the head member 20, thus securing the denture 24 in place.

Any fluid confined in the recess 26 as the head member 20 is being inserted therein finds relief through the groove 22, thus facilitating the entry or insertion of the head member 20 therein. When the head member 20 resides within the elastomeric member 27, the groove 22 provides constant passageway for fluid present therein.

Second Embodiment

In a different version of this invention the groove 22 is positioned on the head member 20 to reside wholly within the elastomeric member 27 opening. The elastomeric member 27 forms an airtight seal around the head member 20 after the head member 20 has passed therethrough, whereby the groove 22 retains a certain amount of fluid 28 which is trapped therein. The trapped fluid 28 provides a cushion to ease the masticatory load on the head member 20. In addition, the trapped fluid 28 increases the retentive force to better secure the denture 24 in place.

Third Embodiment

Figure 5:
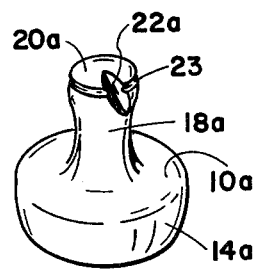
FIG. 5 is a perspective view of a modified dental post embodying the invention.

Referring now to FIG. 5, a modified dental post is generally indicated at 10a and comprises a main body 14a similar to the body 14, having a first stem or post member 16a extending outwardly therefrom in the same manner and for the same purpose as the stem 16. A second stem member 18a extends axially outwardly from the body 14a and in an opposite direction with respect to the stem 16a. A head member 20a is provided on the outer end of the stem 18a and is provided with a groove 22a substantially identical with the groove 22. A second groove 23, provided to increase the cushion area 28, extends around the circumference of the head member, beginning and ending at the groove 22a, forming channels on each side of the groove 22a. Of course, the desired cushioning action to respond to the direction of stress may be provided by selecting the optimum size and cross-sectional configuration for the groove 23.

In use, the dental post 10a functions in substantially the same manner as the post 10, with the exception that the additional annular or circumferential groove 23 increases the fluid trapped and provides greater cushion area when the denture 24 is seated on the dental post 10a.

Fourth Embodiment

Figure 6:
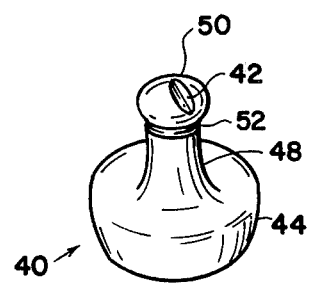
FIG. 6 is a sectional elevational view of another modified dental post embodying the invention.

Turning now to FIG. 6, therein is illustrated another form of the invention. Reference character 40 generally indicates a dental post comprising a main body 44 similar to the body 14 in FIG. 2, and having a stem or post member 46 extending outwardly therefrom in the same direction and for the same purpose as the stem 16. A second stem 48 extends axially outwardly from the body 44 in the same manner and for the same purpose as the stem 18. A head member 50 is provided on the outer end of the stem 48, and the head member 50 is provided with a groove 42 substantially identical with groove 12 and positioned as described and for the same purpose as in the second form of this invention. A circumferential groove 52, configured to engage the denture apparatus elastomeric member 27 and provide anchorage means thereof, is provided adjacent to the junction of the head member 50 and the second stem member 48.

In use, as the head member 50 is being received in the opening in the denture apparatus elastomeric member 27, fluid present in the recess 26 finds relief through the groove 52, thus facilitating the entry or insertion of the head member 50 therein. The circumferential groove 52 is situated to engage the elastomeric member 27 to cause a residual space 54 between the head member 50 and the inner periphery 56 of the recess 26, as shown in FIG. 7. When the circumferential groove 52 engages the elastomeric member 27, an airtight seal is formed, trapping fluid present in the residual space 54 which provides a cushion to ease the masticatory load on the head member 50 and enhances the retentive capabilities of the dental post 40. Of course, the amount of residual space 54 desired to provide particular cushion area may be obtained by positioning the circumferential groove 52 accordingly.

Whereas the present invention has been described in particular relation to the drawings attached hereto, it should be understood that other and further modifications, apart from those shown or suggested herein, may be made within the spirit and scope of this invention.

What is claimed is:

1. A dental post for removably securing a denture to the mandible, the denture apparatus having therein a recess defined in part by an elastomeric member having an opening therethrough, the dental post comprising
   a body portion having a first stem for permanent attachment to the mandible; and
   a second stem portion extending from said body portion in the plane of and exterior of the gingival or gum of the mouth, the second stem portion having an enlarged outer head member dimensioned to be received through a denture apparatus elastomeric member by compression of the elastomeric member whereby the elastomeric member applies retentive force to the head member, the head member having a groove in the exterior surface providing a fluid passageway when the head member passes through the opening in the elastomeric member.

2. A dental post for removably securing a denture to the mandible, the denture apparatus having therein a recess defined in part by an elastomeric member having an opening therethrough, the dental post comprising
   a body portion having a first stem for permanent attachment to the mandible; and
   a second stem portion extending from said body portion in the plane of and exterior of the gingival or gum of the mouth, the second stem portion having an enlarged outer head member dimensioned to be received through a denture apparatus elastomeric member by compression of the elastomeric member whereby the elastomeric member applies retentive force to the second stem, the head member having a groove on the exterior surface providing a fluid passageway when the head member passes through the opening in the elastomeric member, the groove being situated to reside wholly within the elastomeric member, the elastomeric member forming an airtight seal around the head member after the head member has passed therethrough.

3. A dental post as in claim 2 wherein the groove extends in the peripheral space from adjacent the outer end of the head member to adjacent the junction of the head member and the second stem.

4. A dental post as in claim 2 wherein the head member is configured substantially as a segment of a sphere.

5. A dental post as in claim 3 wherein the groove is disposed angularly with regard to the axis of the second stem.

6. A dental post as in claim 2 wherein the groove is provided with a plurality of channels particularly designed to increase the cushion area.

7. A dental post as in claim 6 wherein the channels comprise a circumferential groove beginning and ending at the first-mentioned groove.

8. A dental post for removably securing a denture to the mandible, the denture apparatus having therein a recess defined in part by an elastomeric member having an opening therethrough, the dental post comprising:
   a body portion having a first stem for permanent attachment to the mandible; and
   a second stem portion extending from said body portion in the plane of and exterior the gingival or gum of the mouth, the second stem portion having an enlarged outer head member dimensioned to be received through a denture apparatus elastomeric member by compression of the elastomeric member whereby the elastomeric member applies retentive force to the second stem; the head member having in the exterior surface a groove providing a fluid passageway when the head member passes through the opening in the elastomeric member; the head member in addition, having adjacent to the junction of the head member and the second stem a circumferential groove configured to engage the denture apparatus elastomeric member and provide anchorage thereof and situated to cause a residual recess provided in the denture, whereby the residual space fluid is trapped therein when the circumferential groove engages the elastomeric member forming an airtight seal; the trapped fluid providing a cushion to ease the masticatory load on the head member and enhance the retentive force of the dental post to better secure the denture apparatus.

* * * * *